(12) United States Patent
Vanhove et al.

(10) Patent No.: US 7,394,545 B2
(45) Date of Patent: Jul. 1, 2008

(54) APPARATUS FOR CHARACTERIZING AND MEASURING THE CONCENTRATION OF OPAQUE PARTICLES WITHIN A FLUID SAMPLE

(75) Inventors: Andre Vanhove, Beveren (BE); Brian W. Lasiuk, Spring, TX (US); Peter J. Codella, Niskayuna, NY (US); Wiley Lyle Parker, Conroe, TX (US)

(73) Assignee: GE Betz, Inc., Trevose, PA (US)

( * ) Notice: Subject to any disclaimer, the term of this patent is extended or adjusted under 35 U.S.C. 154(b) by 263 days.

(21) Appl. No.: 11/178,846

(22) Filed: Jul. 11, 2005

(65) Prior Publication Data

US 2007/0008529 A1    Jan. 11, 2007

(51) Int. Cl.
*G01N 21/00* (2006.01)
(52) U.S. Cl. ..................................... 356/441
(58) Field of Classification Search ........................ None
See application file for complete search history.

(56) References Cited

U.S. PATENT DOCUMENTS

| | | | |
|---|---|---|---|
| 3,449,586 A | 6/1969 | Serra | |
| 3,952,580 A | 4/1976 | Bennett | |
| 4,362,386 A * | 12/1982 | Matsushita et al. | 377/10 |
| 4,927,519 A | 5/1990 | Forester | |
| 5,309,213 A | 5/1994 | Desjardins et al. | |
| 5,504,573 A * | 4/1996 | Cheiky-Zelina | 356/70 |
| 7,127,356 B2 * | 10/2006 | Nicoli et al. | 702/26 |

FOREIGN PATENT DOCUMENTS

| | | |
|---|---|---|
| EP | 0 321 424 B1 | 3/1993 |
| EP | 0 529 397 B1 | 7/1995 |
| JP | 06201592 A | 7/1994 |
| JP | 09304412 A | 11/1997 |

* cited by examiner

*Primary Examiner*—Gregory J. Toatley, Jr.
*Assistant Examiner*—Amanda H Merlino
(74) *Attorney, Agent, or Firm*—Wegman, Hessler & Vanderburg

(57) ABSTRACT

A system and method for counting opaque particles within a fluid sample. The system uses an optical lens system to focus a light beam onto a sample on a multi-dimensional translation stage. The translation stage is moved in a pattern such that the intensity of the transmitted light is measured as a function of path length. A photo detector is used to measure the transmitted light through the sample. An analog-to-digital converter quantifies the transmitted light intensity. Changes in light intensity along the path length are correlated with the detection of an opaque particle. Data processing algorithms are implemented to automatically determine the background noise level associated with the acquired data and to set a discriminator level above which a particle is registered. The total number of particles and an areal density is reported along with an estimate of the uncertainty.

7 Claims, 7 Drawing Sheets

APPARATUS FOR CHARACTERIZING AND MEASURING THE CONCENTRATION OF OPAQUE PARTICLES WITHIN A FLUID SAMPLE

FIELD OF THE INVENTION

The present invention relates to systems and methods for characterizing and quantifying a dispersive medium; specifically, measuring the concentration of particles within a fluid sample.

BACKGROUND OF THE INVENTION

Thermal conversion is a process in which, by the application of heat, large hydrocarbon molecules are broken into smaller molecules with a lower boiling point. These operations are carried out in the industry of crude oil refining by plants such as a visbreaker, coker, and hydrocracker for obtaining intermediate or light cuts of higher value, from heavy residues of lower commercial value.

It is well known that the fouling potential of a fluid can be estimated and characterized by the concentration of the dispersed phase, particularly by the concentration of the dispersed phase present in a specific size range. In hydrocarbon systems in particular, it has been recognized that the concentration of asphaltenes (i.e., carbon particles or opaque species) with linear dimension greater than about 1 micron in visbroken tars is a good indication of the fouling potential of the material.

Therefore, there is a need to provide a simplified, automated system and method that can easily be used to carry out optical analysis of visbroken tars and other fluid samples in order to characterize and quantify the concentration of particles within the fluid sample with high accuracy and reproducibility.

SUMMARY OF THE INVENTION

The present invention provides a system and method for counting opaque particles within a fluid sample. The invention does so by measuring the modulation of transmitted light through a fluid sample. The system uses a strongly convergent optical lens system to focus light onto a prepared sample. In the specific embodiment, the optics of a conventional optical microscope are used. A 3-dimensional translation stage is installed downstream of the focusing optics so that the sample can be scanned over a large region, and at a specific focal plane. A photo detector is placed on the opposite side of the stage from the focusing optics to measure the transmitted light through the sample. The photodetector is read-out by an analog-to-digital converter (ADC) in order to provide a digital (i.e., quantitative) measure of the transmitted light intensity. The translation stages are then moved in a pattern, such that the intensity of the transmitted light is measured over a representative area of the sample. When an opaque particle of a threshold size is encountered in the sample, the intensity of the transmitted light is strongly attenuated. Such change of light intensity is then correlated with the detection of an opaque particle. Data processing algorithms are implemented to determine the background noise level associated with the acquired data and to set a threshold level. As such, a specific signal-to-noise ratio can be specified to define when a particle is registered. Size discrimination is achieved according to the physical dimensions of the beam waist of the focused light beam.

DETAILED DESCRIPTION OF THE INVENTION

Figure 1:
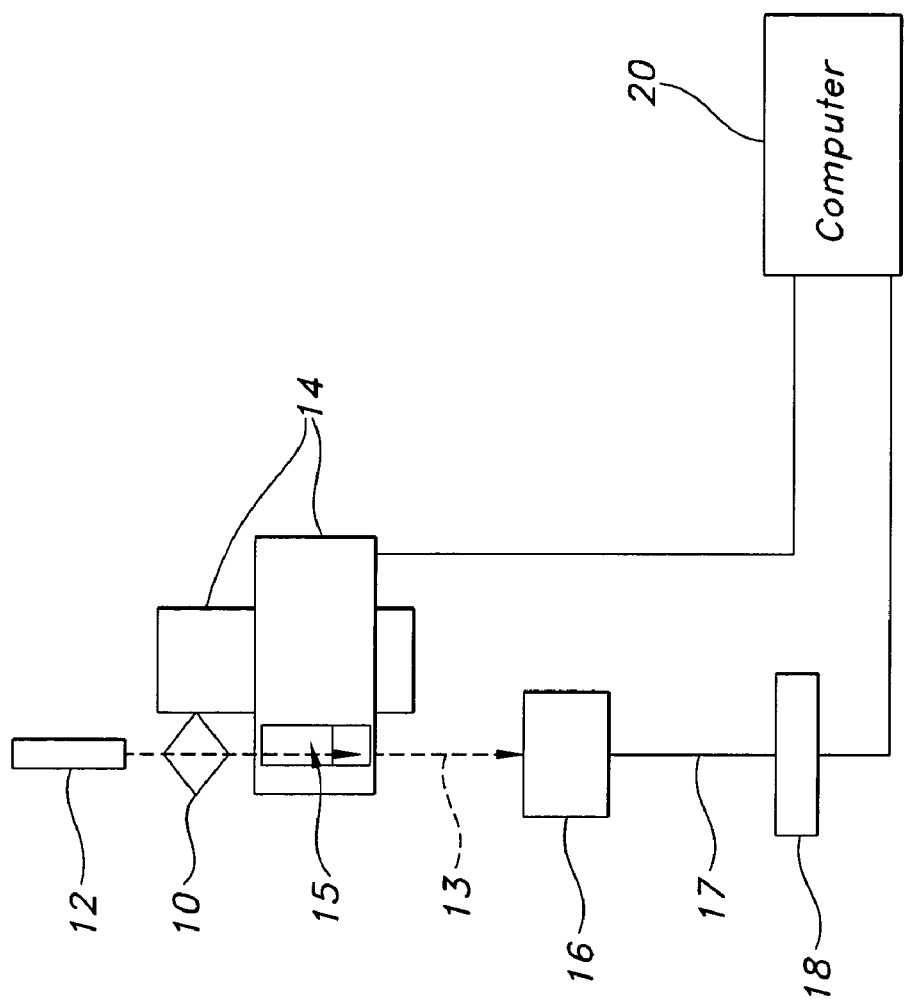
FIG. 1 is a view of the scanning apparatus of the present invention, showing the schematic relationship of the various elements.

Exemplary embodiments and examples describing the present invention will be described below with reference to the accompanying drawings. As shown in FIG. 1, this invention uses an optical system as generally indicated by the number 10, which in the present exemplary embodiment comprises a microscope, a light source 12, and a multi-axis translation stage 14. The light source 12 may be implemented, for example, in the form of a solid state visible laser. An infra-red (IR) laser may also be used, and is in some cases preferable owing to the fact that HC solutions are typically much more transparent to IR light, than visible. The translation stage 14 may be moved horizontally in the x and y directions in response to control signals generated by an associated computer 20 to direct the light beam along a plurality of paths through the sample. The third axis moves the stage vertically, towards and away from the focusing lens. This permits selection of a focal plane within the sample. In another exemplary embodiment, the present invention contemplates providing means for moving the light source 12 with respect to the sample, thereby allowing the light beam to be directed through the sample to achieve the same results. Moreover, the present invention also contemplates usage of a flow cell to receive a flow of sample fluid, wherein the sample fluid flows through the flow cell while the light beam is directed through a portion of the flowing sample. Also implemented is a photodetector 16, for example, a PIN photodiode, located on the opposite side of the stage 14 to detect light 13 being transmitted through the sample volume, which is located on the translation stage. The photodetector 16, in turn, is connected by a connector and cable 17, for example, a twisted pair with BNC connector, to an analog-to-digital (A/D) converter 18 to quantify the transmitted light intensity.

In one exemplary embodiment of the invention, a colloidal fluid sample material of thick viscous tar comprising asphaltene (or carbon based) particles is placed on the translation stage 14. The asphaltene particles within the tar medium are opaque to visible light. The tar medium is also opaque to visible light when the path length through the medium typically exceeds a linear dimension of about 1 cm. A sample volume is dispensed on a slide, or flow cell 15 such that a typical sample thickness of 10-20 microns is produced. As such, the thickness of sample medium should be made thin enough so as to provide a differential transparency between the viscous tar medium and the asphaltene particles in question. In this exemplary embodiment, in order to optimize light transmission from a low power light source, a solid state laser that produces radiation at about 633 nm is chosen. This provides adequate power at a suitable region in the EM (electromagnetic) spectrum to provide transmission through a thin layer of tar, while the carbide particles remain opaque.

Figure 3:
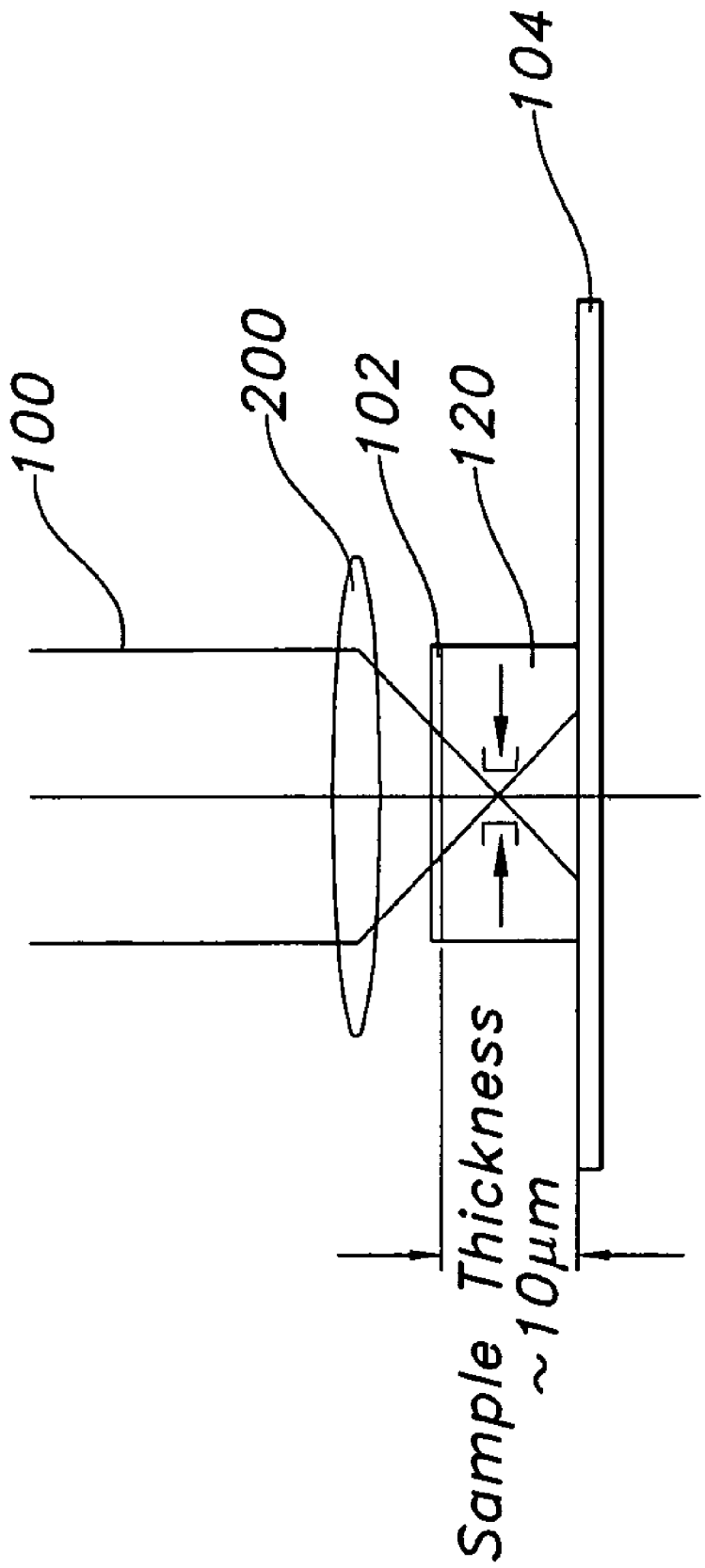
FIG. 3 is a diagram illustrating optics used to convergently focus a light beam to a narrower beam waist.

In order to have sensitivity to the specifically sized particles, appropriate optics should be used to focus the laser light onto the sample. The choice of a monochromatic light source allows the design of the optics to be optimized. As shown in FIG. 3, a highly convergent lens system 200 is used to focus the light beam 100 down to a beam waist of approximately 1 micron. This size determines the minimum size a particle must be to fully attenuate the laser light. If a particle is smaller than 1 micron, it will still allow the transmission of light. As such, the focusing optics define the threshold size for particle detection. An equation for calculating the beam waist is as follows:

$$W = 0.61 \lambda/d$$

Where W=beam waist (1/e) width
λ=wavelength of light
d=numerical aperture
For example, if λ=633 nm and d=0.56, then W=0.7 µm.

Since we are interested in particles larger than 1 micron (and smaller than ~20 microns), we do not use an IR laser, even though the HC solutions are more transparent to IR radiation because the beam waist would increase in size for the given optics. As such, we would reduce the sensitivity of the instrument.

The fluid sample 120 thickness is chosen to be about 10 microns. The beam 100 is focused on the slide 104, below a cover slip 102, or a flow cell in the sample volume. The depth and width of focus are constrained by the optical system and the selected light wavelength. In one exemplary embodiment, both dimensions are selected to be approximately 1 micron.

Figure 2:
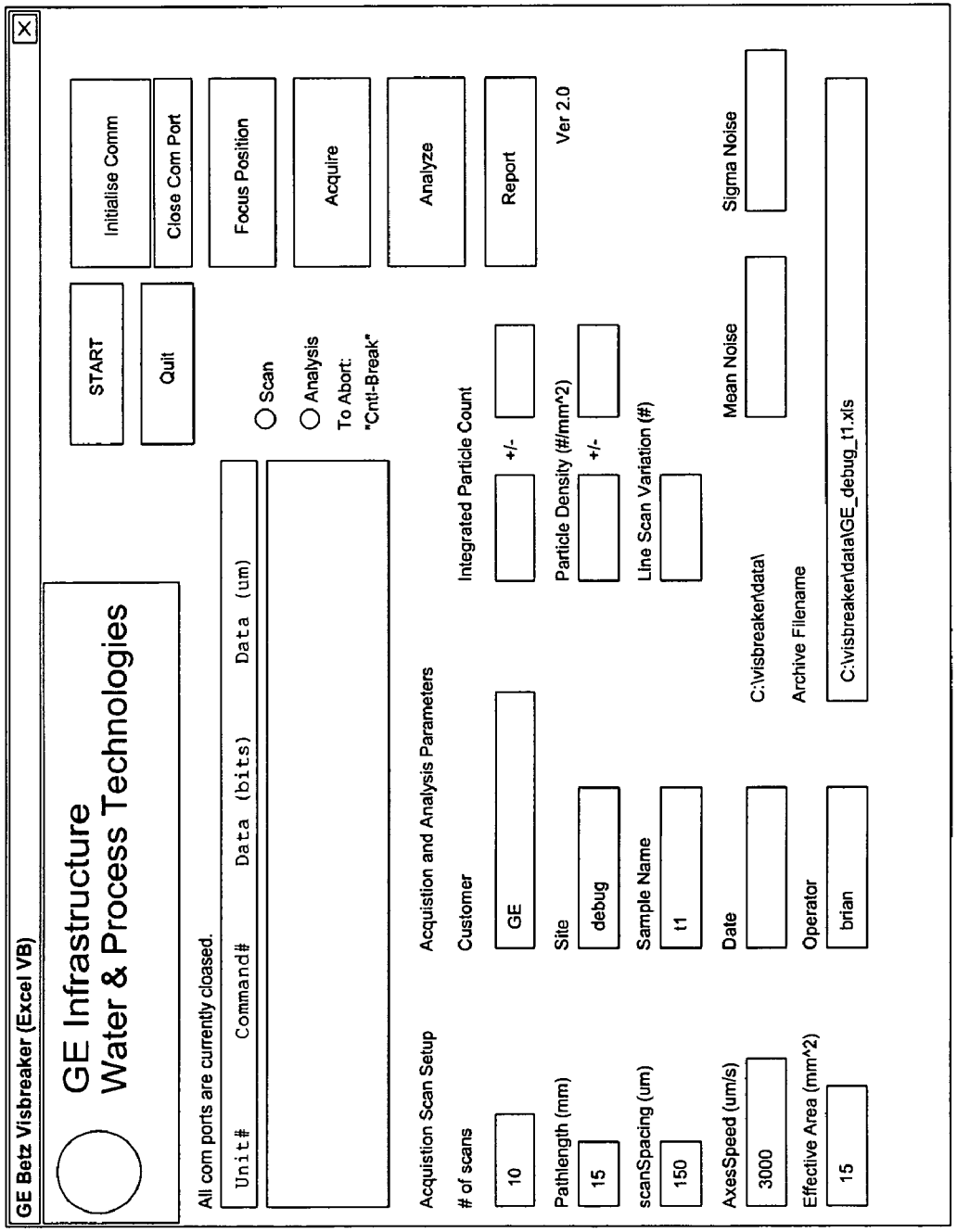
FIG. 2 illustrates an example of a computer screen displaying a data acquisition interface in accordance with the present invention.

FIG. 2 illustrates an example of a screen display presented by the software of the present invention. The screen display illustrated in FIG. 2 represents a data acquisition interface allowing the operator to specify a variety of scanning acquisition, analysis parameters, operating conditions of the instrument, and results of the measurement. The methods by which the operator selects items, inputs data, and otherwise interacts with the data acquisition interface are conventional, and further discussions of these operations are not provided herein. In an exemplary embodiment of the invention, data acquisition software was implemented via Visual Basic® in Excel® with analysis and signal processing code being implemented in GNU Octave, although those skilled in the art of software programming will appreciate that many other software programming means may be used to achieve the same results.

A testing plan was designed and implemented to validate and measure the scanning performance of an exemplary embodiment of the present invention. In particular, measurement repeatability is validated by analyzing the stability of identical measurements. Reproducibility of the data is examined by analyzing the effects of scanning different regions in the sample. This is complicated by the effects of sample homogeneity. Accuracy of the system is tested by comparing the scanning data with visual images and PV (PV=peptization value) of the sample. Precision of results is analyzed for statistical uncertainty with path length and by optimizing sample area, as discussed in more detail below.

Figure 4:
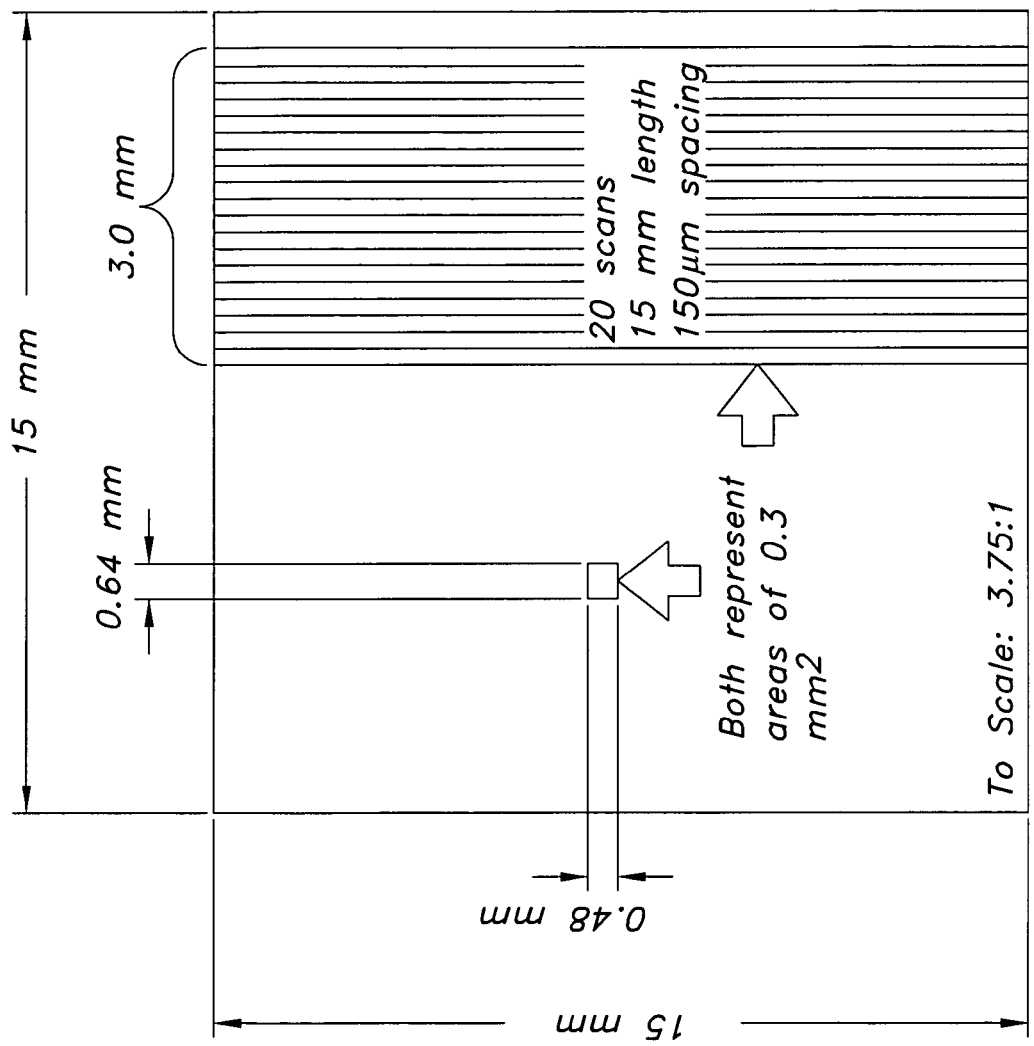
FIG. 4 illustrates a plurality of spaced apart linear scans compared with a solid block representing an equivalent effective surface area.

FIG. 4 illustrates an example of how the scanning system samples a large region of the sample. The array of linear scans (shown on the right side of FIG. 4) represent the same effective surface area as the small box illustrated on the left side of FIG. 4. For example, an array of 20 linear scans of 15 mm length with a 1 micron wide laser beam effectively samples the same area as does the smaller 0.48 mm×0.64 mm box. However, by sampling over a larger area of the sample, the effects of sample inhomogeneity, local fluctuations in the sample, and sample variation are reduced drastically. As such, the statistical results are much more accurate and reproducible.

To demonstrate the repeatability of our scanning results, five identical 15 mm scans from a same sample, covering a 0.015 mm² effective area were measured. The measurement showed that the number of counts per 15 mm line scan were identical within 95% confidence limits. Increasing the sampling region to 20-15 mm scan paths, the same systematic effects were seen. After applying statistical analysis to the results, it was observed that the single line scan measurements are normally distributed, with a standard deviation (σ)=1.6 counts on a mean of 8.0 counts. Furthermore, the total integral count of the sample was 159 with a standard deviation of 9 counts. This shows that both the mean particle count per path, and the total integral particle count were statistically identical and repeatable, over the separate trials, thus demonstrating that instrument stability and repeatability is excellent. It also demonstrates that the fractional error can be reduced by increasing the sampling length. This is due to the fact that independent errors do not add linearly, but in quadrature.

As can be noted from the above data, the system of the present invention is capable of minimizing and quantifying the effects of sample inhomogeneity.

Figure 5:
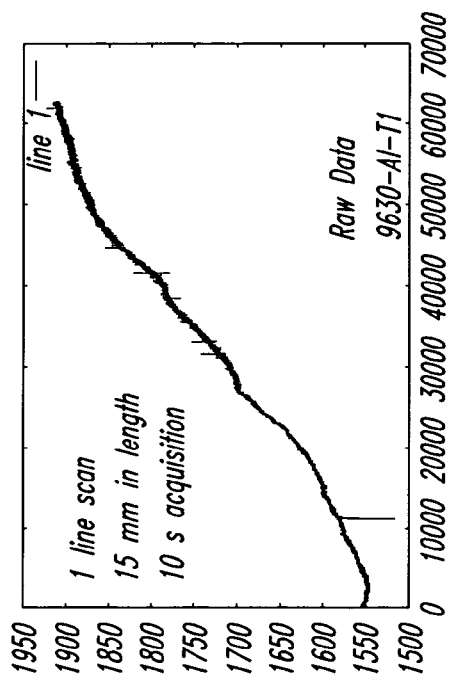
FIG. 5 is a graph illustrating raw data obtained from a single line scan.

Turning now to FIG. 5, there is shown a graph representing exemplary raw data obtained from a single line scan of 15 mm length taken during a 10 second acquisition window.

Figure 6:
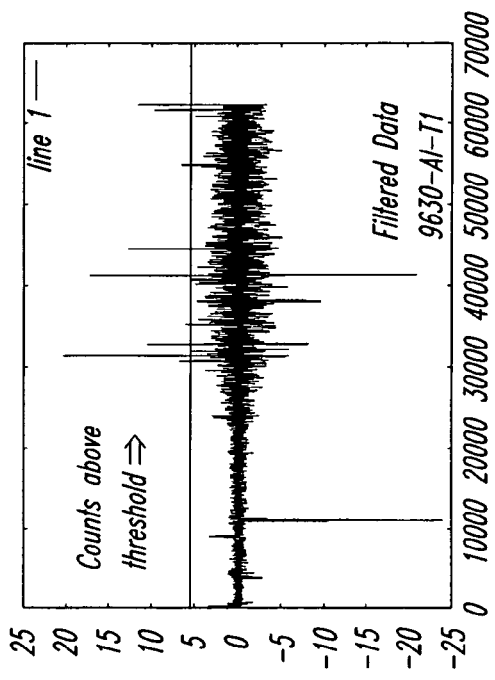
FIG. 6 is a graph illustrating the raw data of FIG. 5 after the data has been filtered to remove line noise and gross intensity variations.

In FIG. 6, the raw data of FIG. 5 is processed by a Fourier filtering to remove 50/60 Hz line noise and a median filter is used to remove gross intensity variations to extract the number of counts above a threshold value. This process may be repeated for all line scans (e.g., 20 line scans) to calculate the total particle areal density of the sample under test. In one example, the number of peak counts from a single line scan is calculated as $$\rho_1 = (9 \pm 3) \div (15 \text{ mm} \times 1 \text{ µm}) = 600 \pm 200 \text{ mm}^{-2}$$

Repeating this calculation for a measurement spanning over 20 paths, the error decreases as shown below:

$$\rho_{tot} = (149 \pm 12) \div (20 \times 15 \text{ mm} \times 1 \text{ µm}) = 497 \pm 40 \text{ mm}^{-2}$$

We see that the error decreases according to Gaussian statistics where the error propagates in quadrature instead of linearly, a well known statistical property.

Figure 7:
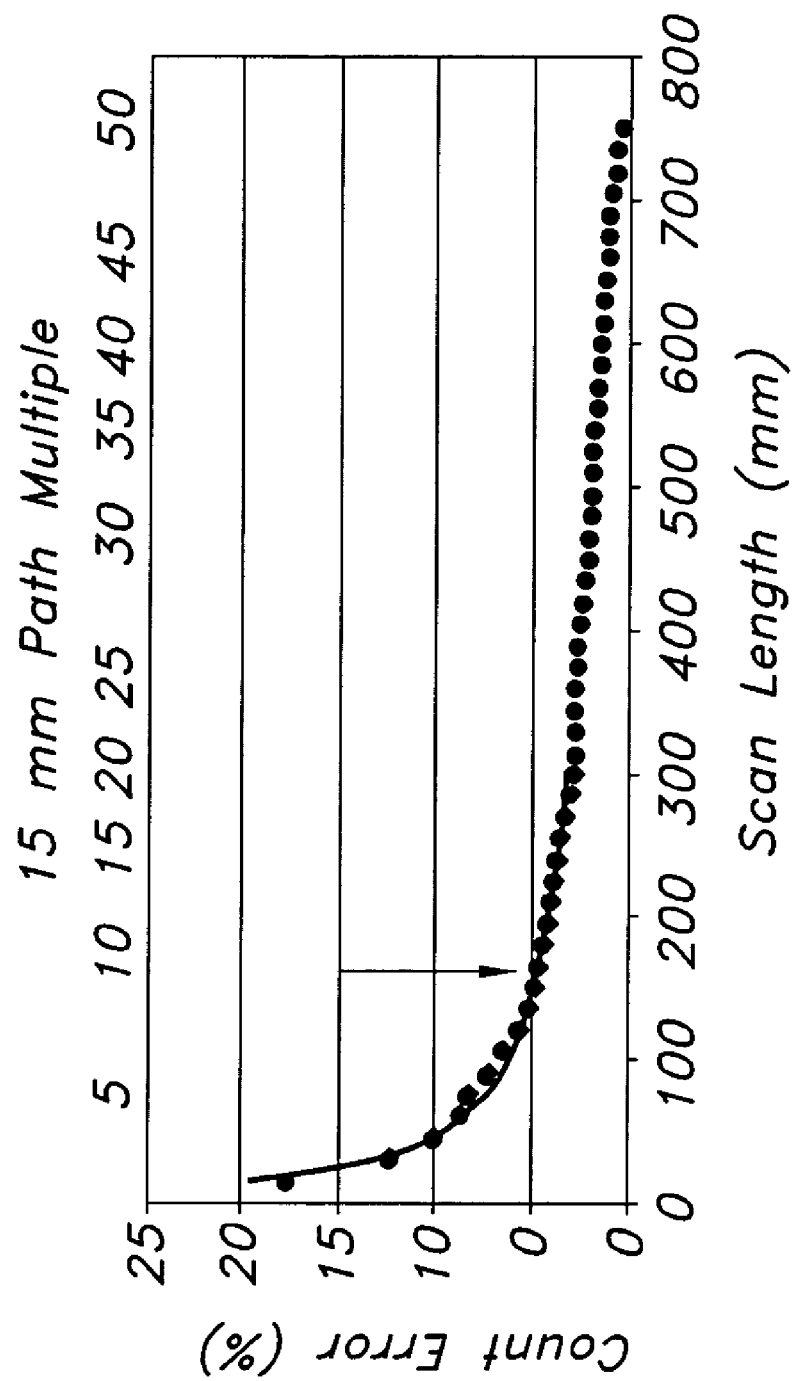
FIG. 7 is a graph illustrating decreasing statistical error as a function of overall scan length.

As shown in FIG. 7, an approximate 5% uncertainty is achieved at 10 line scans of 15 mm length (i.e., 0.15 mm² effective area). Statistical error is thus shown to decrease with $N^{-0.6}$, where N is the number of 15 mm path length multiples. From the exemplary data of FIG. 7, it is shown that an overall path length of about 150 mm (10×15 mm) would achieve an approximate 5% error.

In order to determine the background noise in the signal as in FIGS. 5 and 6, the present invention provides a software algorithm which automatically computes the background noise in the acquired data set and sets a discriminator level to count the number of particles. A measurement of the light transmission is made when no scanning is occurring. Thus, the signal is an estimate of the nominal noise. Calculating the standard deviation of this signal distribution allows the estimate. The value can be used to determine a fixed signal-to-noise ratio on which to accept particles.

In accordance with the present invention, the optical scanning instrument is capable of measuring the number of micron sized particles in a solution, and to quantify the density of such particles in an automated and timely fashion.

To demonstrate the capabilities of the present invention, the following sample specimens, with various concentrations of asphaltenes were used for analysis and validation:

Specimen A: 9630 Asls, PV=1.7, low particle density (highly diluted).
Specimen B: 9630-6, PV=1.4, intermediate particle density (partially diluted).
Specimen C: 9630-7, PV<1.0, high particle density, heavily cracked sample (slightly diluted).
Specimen D: 9630-mod, 13% 9630-7+9630 Asls, PV=about 1.35 (partially diluted).

Figure 8:
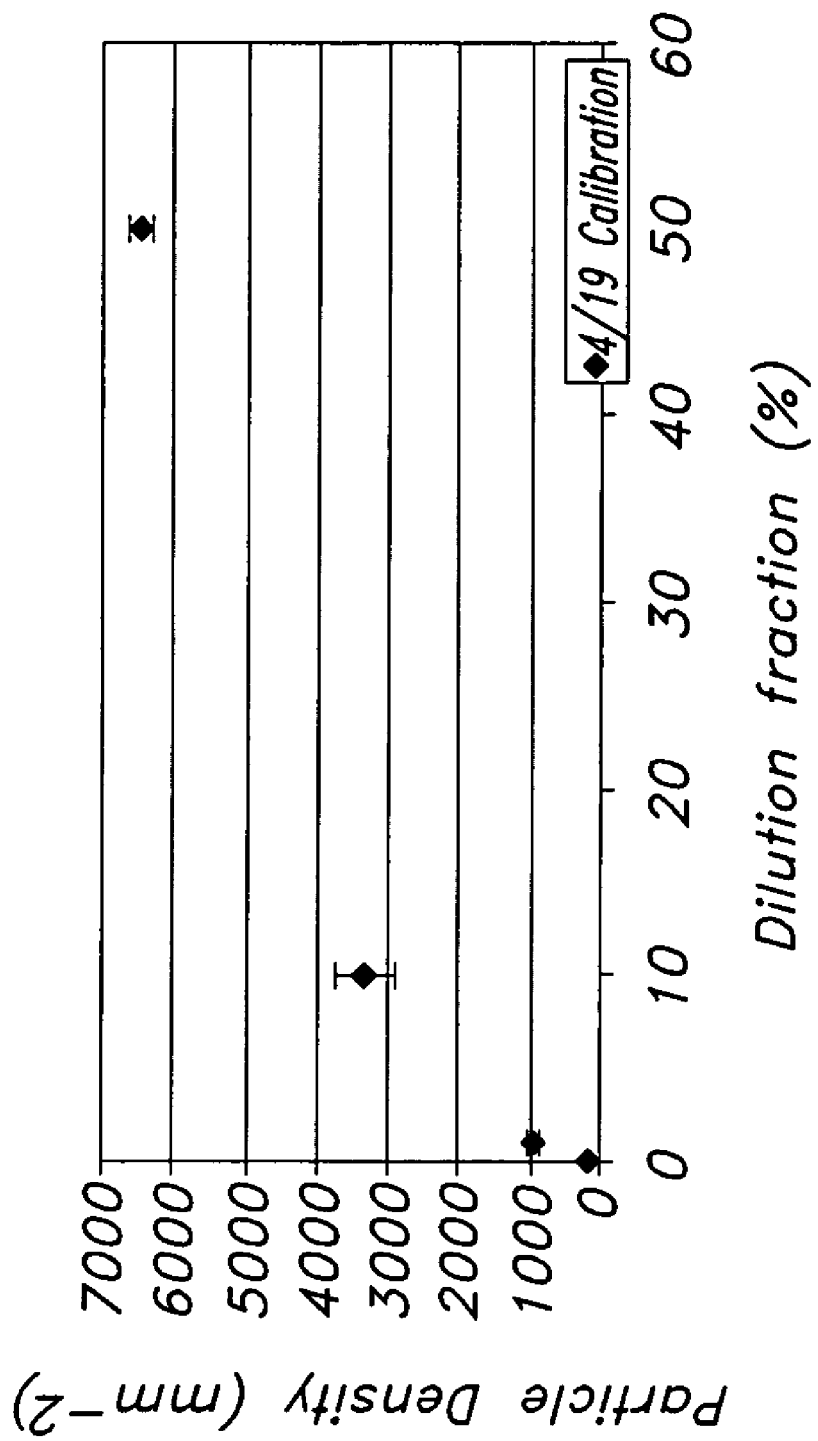
FIG. 8 is a graph showing the correlation of particle density as measured by the instrument to samples with a varying degree of dilution from a fully cracked (i.e., high asphaltene particle density).

The scanning results from these samples were then compared to photographs of the samples, and a correlation was found between the images and the scanned results. A graph showing the correlation of particle density as measured by the instrument to samples with a varying degree of dilution from a fully cracked (i.e., high asphaltene particle density) is shown in FIG. 8.

Overall, the testing results demonstrate that the system of the present invention provides good repeatability and shows correlation with visual image views. It has been shown that a relatively large sample area may be covered with automated operation, thus reducing the effects of local fluctuations in particle density. Data can also be assigned an error to increase precision of results.

While the disclosure has been illustrated and described in typical embodiments, it is not intended to be limited to the details shown, since various modifications and substitutions can be made without departing in any way from the spirit of the present disclosure. As such, further modifications and equivalents of the disclosure herein disclosed may occur to persons skilled in the art using no more than routine experimentation, and all such modifications and equivalents are believed to be within the scope and spirit of the disclosure as defined by the following claims.

What is claimed is:

1. A method for measuring concentration of opaque particles in a fluid, comprising the steps of:
   a. providing an optical lens system comprising a translation stage, said translation stage having three axes of movement;
   b. introducing a sample of said fluid onto said stage, said particles in said fluid having a range of size with diameter less than about 20 microns;
   c. selecting a laser light source that produces a laser light beam with a wavelength effective to transmit through said fluid, but not said particles;
   d. focusing said laser light beam into said sample with a beam waist of said light beam based on the size of said particles;
   e. directing said light beam along a plurality of path lengths across a predetermined area of said sample;
   f. detecting light transmitted through said sample along each said path length;
   g. quantifying the intensity of said transmitted light; and
   h. correlating said quantified transmitted light to a concentration of said particles in said sample.

2. The method of claim 1 wherein said correlating step comprises signal processing algorithms for filtering electronic and stochastic noise.

3. The method of claim 2 wherein a thickness of said sample varies within said predetermined area.

4. The method of claim 1 further comprising the step of determining said predetermined area so as to achieve a desired precision of results.

5. The method of claim 4 further comprising the step of increasing said predetermined area to reduce the effects of inhomogeneity of said sample.

6. The method of claim 1 wherein said translation stage is a flow cell.

7. The method of claim 1 wherein said beam waist has a cross dimension of approximately one micrometer.

* * * * *